United States Patent
Luitjes et al.

(10) Patent No.: US 6,395,810 B1
(45) Date of Patent: May 28, 2002

(54) BICYCLOOCTANE DERIVATIVES AS PLASTICIZERS

(75) Inventors: Hendrikus Luitjes, Putten (NL); Johannes Carolus Jansen, Milan (IT)

(73) Assignee: ATO B.V., Wageningen (NL)

(*) Notice: Subject to any disclaimer, the term of this patent is extended or adjusted under 35 U.S.C. 154(b) by 0 days.

(21) Appl. No.: 09/623,422

(22) PCT Filed: Mar. 4, 1999

(86) PCT No.: PCT/NL99/00115

§ 371 (c)(1),
(2), (4) Date: Oct. 26, 2000

(87) PCT Pub. No.: WO99/45060

PCT Pub. Date: Sep. 10, 1999

(30) Foreign Application Priority Data

Mar. 4, 1998 (NL) .............................................. 1008477

(51) Int. Cl.[7] .............................. C08K 5/15; C08K 5/52; C08K 5/09; C08K 5/12
(52) U.S. Cl. ........................ 524/109; 524/140; 524/296; 524/311; 524/315; 523/218
(58) Field of Search ................................. 524/109, 140, 524/296, 311, 315; 523/218

(56) References Cited

FOREIGN PATENT DOCUMENTS

| | | |
|---|---|---|
| DE | 33 47 075 | 7/1985 |
| GB | 613444 | 11/1948 |
| GB | 953096 | 3/1964 |
| JP | 59 175408 | 10/1984 |
| JP | 06 261774 | 9/1994 |
| WO | WO 96/33689 | 10/1996 |
| WO | WO 96 33689 | * 10/1996 |
| WO | WO 97/26003 | 7/1997 |

OTHER PUBLICATIONS by D. Braun et al., "Polyesters with 1.4:3.6–Dianhydrosorbitol as polymeric plasticizers for PVC", *Applied Macromolecular Chemistry and Physics*, vol. 199, Aug. 1992, pp. 191–205.

by D. Abenhaim et al., Selective alkylations of 1,4:3,6–dianhydro–D–glucitol (isosorbide), *Carbohydrate Research*, vol. 261, No. 2, Aug. 1994, pp. 255–266.

* cited by examiner

*Primary Examiner*—Kriellion A. Sanders
(74) *Attorney, Agent, or Firm*—Young & Thompson

(57) ABSTRACT

The use of isosorbide esters, isosorbide polyesters, isosorbide ethers, isosorbide carbonates, isosorbide thioethers, isosorbide thioesters, isosorbide amides, isosorbide (thio) urethanes, isosorbide urea, isosorbide phosphates and isosorbide phosphonates as a plasticizer is described. Instead of isosorbide it is also possible for corresponding diols such as isomannide and similar compounds, in which the ring oxygen atoms of the isosorbide have been replaced by carbon or by other heteroatoms, to serve as a base. In particular, this relates to $C_3$–$C_{11}$ alkanoates of isosorbide, isomannide and the like. In particular, the compounds are used as a plasticizer in poly(vinylchloride), optionally in conjunction with usual plasticizers such as dioctyl phthalates.

11 Claims, No Drawings

BICYCLOOCTANE DERIVATIVES AS PLASTICIZERS

The invention relates to the use of bicyclo[3.3.0]octane derivatives as plasticisers or solvents for polymers. including thermoplastics.

Plasticisers are indispensable components for thermoplastic materials such as poly(vinyl chloride), and other polymer systems. The most commonly used plasticisers are diesters of dicarboxylic acids, among which the phthalic acid diesters are frontrunners in the plasticiser market with 89%, about half of which is made up of the isomeric diisooctyl esters. Whilst the existing plasticisers are generally satisfactory, there is a need for the range of plasticisers to be extended. Moreover. the existing plasticisers are virtually without exception based on petroleum products, whereas it is desirable for these to be replaced. as far as possible, by renewable raw materials. From an environmental and health point of view it is likewise desirable for dialkyl phthalates to be replaced.

Polyesters based on isosorbide and dicarboxylic acids (adipic acid, suberic acid, sebacic acid and dodecanedioic acid) having molecular weights above 10,000 have been suggested by Braun and Bergmann (*Angew. Makromol. Chem.* 199 (1992), 191–205) as plasticisers for PVC. JP-A-8-173788 describes the use of fatty acid diesters of sorbitans and isosorbide as an emulsifier. JP-A-59-175408 discloses the cosmetic use of esters of isosorbide with fatty acids having more than 8 carbon atoms. WO 96/33689 describes the use of a plasticising solvent, including dimethyl isosorbide, in film-forming water-in-oil emulsions for use in cosmetics.

We have now found that esters and ethers based on isosorbide and analogous derivatives having a low molecular weight have excellent characteristics as plasticisers and solvents for polymer materials. The derivatives are defined in the appended claims. The central unit of these derivatives is a bicyclo[3.3.0]octane-4,8-diyl system, whose carbon atoms in the 2- and 6- position may be replaced by a heteroatom, such as sulphur and in particular oxygen. The attachment of side chains in the 4- and 8- positions can take the form of an ether, ester, (thio)carbonate. thioether, thioester, amide, (thio)-urethane, urea, phosphate or phosphonate. Esters are preferred, but carbonates, urethanes and especially ethers can also advantageously be used. Phosphates and phosphonates are preferred when in addition to the plasticising effect a flame retardant effect is desired.

The side chains thus attached are preferably medium-length alkyl groups. Medium length means at least 3 carbon atoms. preferably at least 4 carbon atoms, especially (for ethers) at least 6 carbon atoms, up to 10 or even 12 carbon atoms. Where reference is made to alkyl, alkenyl etc., these terms include both linear and branched groups. depending on the particular use. branched groups, e.g. isobutyl, isooctyl, isononyl, 2-ethylhexyl and the corresponding acyl groups, or unbranched groups may be preferred. Examples of suitable alkanoyl groups include butanoyl, hexanoyl, 2-ethyl-hexanoyl, octanoyl, decanoyl, and unsaturated groups such as benz(o)yl and undecenoyl. Mixtures of alkyl groups are suitable as well, their average chain length is preferably $C_4$–$C_{12}$.

It is also possible for oligoester side groups of a diacid and a diol, for example succinic acid, which may or may not be substituted. and isosorbide, or of a hydroxy acid such as hydroxystearic acid or caprolactone, to be attached, with an alkyl or alkanoyl group as the terminal group. The chain length of such oligomeric side groups is 1–20, preferably 1–10, most preferably 1–5 repeating units on either side of the central unit, with molecular weights preferably between about 600 and 2000.

The derivatives according to the invention can be prepared in a manner known per se. Derivatives where X represents an oxygen atom in formula 1 can be prepared starting from isosorbide or the isomeric dianhydrohexitols such as isomannide and isoidide. The dianhydrohexitols can in turn be obtained from the corresponding monosaccharides (glucose, mannose) and di- and polysaccharides (sucrose, maltose, lactose, starch, cellulose, galactomannans and the like). Derivatives where one of the atoms X is a nitrogen or a sulphur atom can be prepared in a similar manner from a suitable amino or thio sugar. Derivatives where both atoms X are sulphur atoms can be prepared starting from 1,4-dithiapentalen-3-one which, by reduction and addition, can be converted into a 4,8-disubstituted 2,6-dithiabicyclooctane. Derivatives where one of the groups Y contains a nitrogen or sulphur atom can be obtained from the corresponding 2-amino- or 2-thio sugars, such as a hydrolysis product of chitin. The side chains can be introduced by esterification (eg. using a reactive carboxylic acid derivative), etherification, isocyanate addition, and the like. Polyester side groups can be introduced in a manner known per se, by polycondensation of the suitable dicarboxylic acids and diols or hydroxy acids.

The derivatives according to the invention can be worked into polymer materials in a manner known per se. In general, the polymer and the plasticiser can be mixed in a ratio of between 100:1 and 1:9. The ratio is preferably from 10:1 to 10:8. In addition to the plasticisers or plasticising solvents according to the invention, other customary components are used such as stabilisers, flow improvers, pigments, antioxidants, UV absorbers, flame retardants. fillers, oligomeric or polymeric resins or varnishes, reactive monomers, activators, starters, desiccants, lubricants, waxes. solvents, biocides and the like. This may involve, for example, organic compounds of calcium. magnesium, zinc or barium, β-diketo compounds, β-ketoesters, β-aminocrotonates, uracil derivatives, dihydropyridine derivatives, sterically hindered phenols, sterically hindered amines, phosphites, polyols and hydrotalcites. It is also possible, advantageously, for the plasticisers according to the invention to be combined with known plasticisers such as dialkyl phthalates, dialkyl adipates, dialkyl azelates and dialkyl sebacates, alkylbenzyl phthalates, trialkyl trimellitates, triaryl phosphates, citric acid esters, alkyl benzoates and polyesters based on adipic acid or azelaic acid, and thus for an optimal combination to be achieved in terms of compatibility, renewability, degradability, and plasticising properties.

The derivatives according to the invention can be used for plasticising and/or solubilising any polymer systems, including thermoplasts (PVC etc.), rubbers, inks, coatings, adhesives, sealants. foams and thermosetting resins.

Examples of the use as plasticiser are given below. The plasticisers are used in a manner known for plasticisers and plasticising solvents, as described e.g. in: I. Skeist (ed.), Handbook of Adhesives. 3rd ed., Van Nostrand Reinhold, NY (1990), and H. F. Mark, Encyclopedia of polymer Science and Engineering, 2nd ed., NY (1985). Sealants: The derivatives of the invention can be used as a plasticiser in sealants and caulks, for example in a one or two-component polysulphide sealant or in acrylates or polysiloxanes or natural or synthetic rubbers. In addition to the plasticisers, other components may used in a sealant: epoxidised unsaturated oil (soy, fish, linseed oil), inorganic pigments, desiccants, fillers, and activators such as silica, calcium carbonate, titanium dioxide, lime, zeolites, and adhesion aids, such as organosilicon compounds, and aqueous or organic solvents).

| | |
|---|---|
| 50% liquid polysulphide polymer | 30–70% |
| 4% epoxidised soya oil | 0–10% |
| 2% silica | 0–5% |
| 22% titanium dioxide | general: inorganic pigment 1–25% in general: fillers, activators etc. 1–15% |
| 5% calcium carbonate | |
| 2% lime | |
| 2% zeotite | |
| 4% calcium peroxide (curing agent) | 1–10% |
| 2% plasticiser according to the invention | 1–20% |
| 1% 3-aminopropyltriethoxysilane | 0.1–2.5% |
| Remainder: toluene | |

Printing inks: The derivatives of the invention can be used as plasticiser or solvent in printing ink formulations for application in letterpress (relief), gravure (intaglio), offset lithography (planographic), screen (stencil), electrostatic (reprography) and jet (ink spray) printing. Suitable polymer systems for printing inks include acrylates, rosins, polyamides, polyesters, hydrocarbon resins, alkyd resins, nitrocellulose, cellulose acetates, etc.

| Example of flexographic ink formulation (phr = parts per hundred): | |
|---|---|
| 35 phr titanium dioxide | 5–45% |
| 12 phr polyamide resin | 5–25% |
| 2 phr nitrocellulose | 1–10% |
| 3 phr plasticiser of the invention | 2–20% |
| 5 phr isopropyl acetate | general: |
| 43 phr isopropanol | 20–60% solvent |
| Example of gravure ink formulation: | |
| 10 phr organic pigment or dye | 1–15% |
| 5 phr inorganic extender | 1–20% |
| 5 phr plasticiser of the invention | 2–20% |
| 12 phr acrylic varnish | general: |
| 38 phr nitrocellulose varnish | varnish 20–80% |
| 5 phr wax compound | 2–8% |
| 15 phr ethanol | general: |
| 10 phr isopropyl acetate | solvent 5–35% |
| Example of gravure ink formulation: | |
| 12 phr organic pigment | 1–15% |
| 10 phr titanium dioxide | general: inorganic pigment 1–20% |
| 4 phr plasticiser of the invention | 2–20% |
| 15 phr maleic varnish | general: |
| 40 phr nitrocellulose varnish | varnish 20–80% |
| 4 phr polyethylene wax | 2–8% |
| 10 phr ethanol | general: |
| 5 phr isopropyl acetate | solvent 5–35% |
| Example of screen-printing ink formulation | |
| 3 phr organic pigment | 2–20% |
| 25 phr talc | 5–40% |
| 36 phr acrylated monomer | general: |
| 26 phr 1,6-hexanediol diacrylate | reactive monomer 40–75% |
| 10 benzophenone | general: initiator 1–15% |
| 3 phr plasticiser of the invention | 1–20% |

Adhesives and coatings: The derivatives of the invention can be used as plasticisers in adhesives. Their function is to improve the flexibility, wetting properties and water resistance. The derivatives of the invention are applied as plasticiser for adhesives and sealants of the following classes: natural rubber; synthetic rubber, e.g. butyl, nitrile, neoprene, isoprene, styrene-butadiene rubber and copolymers thereof; carboxylated rubber and carboxyl functional polymers, e.g. and acrylic acid polymers and copolymers; phenolic and amino resin (e.g. urea, melamine); polysulphide resins and adhesives; epoxy resins and adhesives; polyurethanes and isocyanate-functional adhesives; polyvinyl alcohol and polyvinyl acetate and acetal adhesives; acrylate, cyanoacrylate and acrylic acid adhesives and their copolymers; polyester and polyamide; silicone adhesives The types of adhesives include: reactive one-and two component adhesives; hot-melt adhesives; delayed-tack adhesives; solution adhesives; in particular pressure-sensitive adhesives.

Example: two-component vinyl flooring adhesive

| | general: |
|---|---|
| Part A: | |
| 212.5 phr hydrocarbon resin | resin |
| 37.5 phr mineral spirit | solvent |
| 12.5 phr plasticiser of the invention | plasticiser |
| 12.5 phr methanol | solvent |
| 7.5 phr nonionic surfactant | surfactant |
| 50 phr clay | filler |
| Part B: | |
| 100 phr high-solids SBR latex | latex/polymer |
| 0.5 phr phosphate stabiliser | |
| 0.5 phr potassium hydroxide | |
| 0.1 phr defoamer | |
| Water to total solids content 60% | water |

Rubbers and thermoplastic elastomers: The plasticisers of the invention can be used as plasticisers in cured or non-cured natural and synthetic rubbers, and in thermoplastic elastomers. These include all common rubbers, in particular acrylonitrile butadiene rubber (NBR), chloroprene rubber (CR), styrene butadiene rubber (SBR), polybutadiene (BR), 1 to 100 parts, in particular, 5–30 parts. The derivatives are used for decreasing the glass temperature of the rubber and for increasing tensile strength and strength on rupture.
Thermosets: The plasticisers of the invention can be used as plasticisers in thermosetting resins (e.g. polyesters, amino resins) in order to improve the toughness and elongation.
Foams: The derivatives of the invention can also be used as plasticisers in polymeric foams, in particular polyurethane, polyether and latex (natural or synthetic rubber) foams. They can be used to increase compression strength of the foam, refine the cell structure, improve its insulation resistance and increase its tenacity or other chemical, physical or mechanical properties.

EXAMPLE 1

Preparation of Isosorbide Dioctanoate (ISDO)

In a 500 ml flask, provided with a Dean-Stark apparatus, a solution of 25 g (0.171 mol) of isosorbide, 54 g of n-octanoic acid (0.375 mol) and 1.0 g of p-toluenesulphonic acid was boiled for 2 hours in 130 ml of xylene. After cooling, 250 ml of diethyl ether were added and the solution was washed with 1225 ml of 0.1 M NaOH and then with water until the water phase remained neutral. The organic phase was evaporated, whereupon 65 g (95%) of product were isolated.

$^{13}$C-NMR ($\delta$, ppm, CDCl$_3$): 13.9 (—CH$_3$), 22.5+24.7+28.8+31.1+31.5+33.8+70.2+73.3 (—CH$_2$—), 73.6+77.7 (CHO), 80.6+85.8 (CHOR), 172.7 (OCO).

EXAMPLES 2–5

Preparation of Isosorbide Dibutanoate (ISDB) Isosorbide Dihexanoate (ISDH) and Isosorbide bis (2-ethylhexanoate) (ISDEH) and Isomannide Dioctanoate (IMDO)

Using the method of Example 1, starting from the appropriate alkanoic acids and dianhydrohexitols, the title compounds were obtained:

ISB: Yield 87%, $^{13}$C-NMR: 13.3(—CH$_3$), 18.1+35.5+70.2+73.0 (—CH$_2$—), 73.6+77.6 (CHO), 80.5+85.7 (CHOR), 172.1 (OCO).

ISH: Yield 86%, $^{13}$C-NMR: 13.5 (—CH$_3$), 22.0+24.2+31.0+33.7+70.1+73.0 (—CH$_2$—), 73.6+77.6 (CHO), 80.5+85.7 (CHOR), 172.1 (OCO).

ISEH: Yield 89%, $^{13}$C-NMR: 11.5+13.6 (—CH$_3$), 22.4+25.1+29.1+31.4+70.4+73.0 (—CH$_2$—), 46.7 (—CH—), 73.4+77.5 (CHO), 80.5+85.9 (CHOR), 174.8 (OCO).

IMO: Yield 91%, $^{13}$C-NMR: 14.0 (—CH$_3$), 22.5+24.8+28.8+28.9+31.6+33.9+70.4 (—CH$_2$—), 73.5 (CHO), 80.3 (CHOR), 173.2 (OCO).

EXAMPLE 6

Preparation of Plasticised PVC

A two-roll calender was used to make a film from the PVC compound at 142° C., followed by determination of the glass transition temperature (Tg) by means of DMTA (Dynamic-mechanical thermal analysis).

100 parts of PVC 50 parts of plasticiser according to Example 1

1.0 part of hydrotalcite 0.3 part of zinc laurate 0.3 part of calcium stearate

The Tg was 0° C.; that of non-plasticised PVC that otherwise had the same composition was 80° C., and that of PVC plasticised with the same amount of dioctyl phthalate (DOP) was −13° C. The modulus of elasticity at −20° C. was 10$^9$ Pa, at 40° C. 10$^7$ Pa and at 100° C. 3.10$^6$ Pa, values comparable to those of PVC plasticised with DOP.

EXAMPLE 7

Preparation of Plasticised PVC

A film obtained according to Example 6 on the basis of the following compounds:

100 parts of PVC

30–50 parts of plasticiser according to Examples 1–5

1.0 part of hydrotalcite 0.3 part of zinc laurate 0.3 part of calcium stearate was made into small rods whose glass transition temperature was determined by means of DMTA and whose modulus of elasticity and breaking behaviour were determined on a tensile testing machine. The results—as yet not optimised—were compared with those of dibutyl phthalate (DBP) and dioctyl phthalate (DOP) and are shown in Table 1:

TABLE 1

| plasticiser | amount (phr) | Tg (E"max) (° C.) | E (Mpa) at T = 17.6° C. | breaking tension (MPa) | breaking elongation (%) |
| --- | --- | --- | --- | --- | --- |
| ISDB | 30 | 25 | 670 | 28 | 165 |
| ISDH | 30 | 21 | 310 | 26 | 142 |
| ISDEH | 30 | 26 | n.d. | n.d. | n.d. |
| ISDO | 30 | 18 | 600 | 24 | 135 |
| IDMO | 30 | 27 | 390 | 29 | 207 |
| DBP | 30 | 14 | 110 | 18 | 159 |
| DOP | 30 | 23 | 240 | 17 | 130 |
| ISDB | 50 | 2 | 12 | 18 | 193 |
| ISDH | 50 | −7 | 14 | 10 | 149 |
| ISDEH | 50 | −5 | 11 | 11 | 234 |
| ISDO | 50 | −9 | 15 | 18 | 228 |
| IMDO | 50 | −20 | 26 | 15 | 152 |

TABLE 1-continued

| plasticiser | amount (phr) | Tg (E"max) (° C.) | E (Mpa) at T = 17.6° C. | breaking tension (MPa) | breaking elongation (%) |
| --- | --- | --- | --- | --- | --- |
| DBP | 50 | −16 | 7 | 13 | 237 |
| DOP | 50 | −13 | 21 | 14 | 205 |
| none | — | 85 | n.d. | n.d. | n.d. | n.d. = not detetmined

EXAMPLE 8

Preparation of Plasticised NBR

To a commercial acrylonitrile-butadiene rubber (NBR) compound containing carbon black, stabilisers. crosslinkers and further conventional additives was added 20 phr of plasticiser according to the invention (isosorbide bis(2-ethylhexanoate ISDEH) 40° C. After extensive mixing, the mixture was vulcanised at 170° C. in a die having dimensions of 180×120×1 mm. The vulcanisation time was 7 minutes. The vulcanised material was conditioned at 50% relative humidity for two days and punched in accordance with ISO 37. The mechanical properties were determined using a tensile strength tester (Zwick Z010). The E-modulus was determined at 1 mm/min, the other properties at 500 mm/min, in accordance with ISO 12184. Table 2 shows the results, with standard deviations in parentheses.

TABLE 2

| Property | without plasticiser | 20 phr DOP | 20 phr ISDEH | unit |
| --- | --- | --- | --- | --- |
| E-modulus | 7 (1) | 2 (0) | 3 (0) | N/mm$^2$ |
| Stress at 100% strain | 4.2 (0.1) | 1.5 (0.1) | 1.6 (0.2) | N/mm$^2$ |
| Stress at 300% strain | 15.1 (0.5) | 7.1 (0.3) | 7.7 (0.4) | N/mm$^2$ |
| Stress at break | 15.4 (1.8) | 13.0 (1.4) | 13.0 (0.8) | N/mm$^2$ |
| Strain at break | 354 (49) | 499 (38) | 469 (26) | % |

What is claimed is:

1. A process for plasticizing or dissolving a polymer, comprising contacting a polymer with a bicyclo[3.3.0] octane derivative having formula 1:

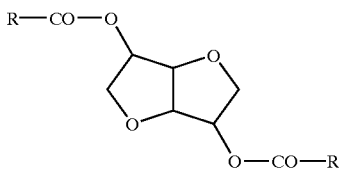

wherein R represents C$_5$–C$_{10}$ alkyl or alkenyl.

2. A process according to claim 1, wherein 1–900 parts by weight of the bicyclooctane derivative are used per 100 parts of synthetic polymer to be plasticised.

3. A process according to claim 1, wherein a dialkyl phthalate, adipate or sebacate, or trialkyl trimellitate, phosphate, citrate and/or a polyester are also used.

4. A process according to claim 1, wherein said polymer is PVC.

5. A process according to claim 1, wherein said polymer is a rubber.

6. A process according to claim 1, for plasticising coatings or adhesives.

7. A process according to claim 1, for plasticising an ink.

8. A process according to claim 1, for plasticising a sealant.

9. A process according to claim 1, for plasticising a polymer foam.

10. Mixture of plasticisers which comprises 20–90 wt % of a bicyclo[3.3.0]octane derivative as defined in claim 1 and 10–80 wt % of at least one of a dialkyl phthalate, adipate, sebacate, or a trialkyl trimellitate, phosphate, citrate, an alkyl benzoate or a polyester.

11. A plasticized polymer comprising 1–900 parts by weight of a bicyclooctane derivative according to claim 1 per 100 parts of a synthetic polymer.

* * * * *